US005716606A

United States Patent [19]
Boyce et al.

[11] Patent Number: 5,716,606
[45] Date of Patent: Feb. 10, 1998

[54] LOTION-BASED SULFUR PREPARATION FOR SKIN TREATMENT

[76] Inventors: Reginald D. Boyce, 2882 Hosta Dr., Charlotte, N.C. 28269; David L. Phillips, 1054 White Plains Rd., Charlotte, N.C. 28213

[21] Appl. No.: 518,965

[22] Filed: Aug. 24, 1995

[51] Int. Cl.[6] .............................. A61K 7/00; A61K 33/04
[52] U.S. Cl. ...................... 424/70.5; 424/703; 424/705; 424/401
[58] Field of Search .................... 424/195.1, 637, 424/401, 70.5, 703, 705; 514/858, 859, 861, 863, 886, 864, 887, 944, 969, 951

[56] References Cited

U.S. PATENT DOCUMENTS

| | | | |
|---|---|---|---|
| 2,884,352 | 3/1959 | Brenner | 167/20 |
| 4,520,012 | 5/1985 | Alfonsi | 424/95 |
| 4,849,214 | 7/1989 | Ruiseco | 424/74 |
| 5,378,461 | 1/1995 | Neigut | 424/94.1 |

FOREIGN PATENT DOCUMENTS 964444  11/1961  United Kingdom .

OTHER PUBLICATIONS

Marcus A. Krupp, M.D. and Milton J. Chatton, M.D., *Current Medical Diagnosis & Treatment 1978*, "Inorganic Pharmaceutical Chemistry", p. 389 (undated).

Marcus A. Krupp, M.D. and Milton J. Chatton, M.D., *Current Medical Diagnosis & Treatment 1978*, "Acne Products—Sulfur Preparations", Feb. 1989, p. 545a.

Marcus A. Krupp, M.D. and Milton J. Chatton, M.D., *Current Medical Diagnosis & Treatment 1978*, "Chapter 3. Skin & Appendages", pp. 74–75 (undated).

*Primary Examiner*—Joseph L. Schofer
*Assistant Examiner*—Sharon Howard
*Attorney, Agent, or Firm*—Kennedy Covington Lobdell & Hickman, LLP

[57] ABSTRACT

A topical composition for treatment of dermatitic conditions, particularly keloids and hypertrophic scars, is provided which comprises sulfur of at least approximately forty weight percent in a spreadable carrier base.

11 Claims, No Drawings

LOTION-BASED SULFUR PREPARATION FOR SKIN TREATMENT

BACKGROUND OF THE INVENTION

The present invention relates generally to preparations for treating the skin and, more particularly, to a preparation for treatment of the skin that contains a high concentration of sulfur.

Sulfur is known to have properties that aid in the treatment of dermatitic conditions. It is employed in various forms for its germicidal, fungicidal, and keratolytic actions. However, current applications of sulfur to treat dermatitic conditions maintain a very low weight percentage of sulfur in the composition. For example, Fostex Medicated Coverup, manufactured by Westwood, is an acne cream that contains only two percent sulfur. Liquimat, manufactured by Owen/Allercreme, is a lotion for treatment of acne that contains only five percent sulfur. Xerac, manufactured by Person & Covey, is a gel for the treatment of acne that contains only four percent of a microcrystalline sulfur. While these compositions do provide for treatment of dermatitic conditions, they use relatively small percentages of sulfur.

In U.S. Pat. No. 4,520,012, issued to Alfonsi, flowers of sulfur, also known as sublimed sulfur, is used in a composition for topical application to improve hair growth. The Alfonsi patent uses a concentration of sulfur of between one and three weight percent and teaches away from the use of any greater concentration of sulfur by stating that greater concentrations do not result in improvement of the effectiveness of the composition.

SUMMARY OF THE INVENTION

It is an object of the present invention to use flowers of sulfur in a percentage greater than that currently used in the industry to provide effective treatment of dermatitic conditions such as skin bumps or razor burn.

Briefly summarized, the present invention uses flowers of sulfur in a spreadable carrier base, the composition being at least approximately forty weight percent sulfur. The preparation is topically applied to treat dermatitic conditions, such as skin bumps or razor burn.

DETAILED DESCRIPTION OF THE PREFERRED EMBODIMENT

In a preferred embodiment, flowers of sulfur is combined with Lubriderm lotion to result in a preparation that is approximately fifty weight percent sulfur. This preparation is noted to be effective in treating different dermatitic conditions. Slightly different preparations have also been evaluated, with similar results. The chemical composition of different preparations tested are presented in Table 1.

TABLE 1

| Chemical Composition of Preparations | | | |
|---|---|---|---|
| | % By Weight | | |
| Preparation | 1 | 2 | 3 |
| Stearic Acid | 0.8 | 0.8 | 0.96 |
| Bayberry Substitute | 0.5 | 0.5 | 0.6 |
| #9 Mineral Oil | 1.05 | 1.05 | 1.26 |
| Spermicetti | 0.5 | 0.5 | 0.6 |
| Lanolin Alcohol | 2.6 | 2.6 | 3.12 |

TABLE 1-continued

| Chemical Composition of Preparations | | | |
|---|---|---|---|
| | % By Weight | | |
| Preparation | 1 | 2 | 3 |
| Jojoba Oil | 1.05 | 1.05 | 1.26 |
| Glycerol Monostearate (SE) | 1.05 | 1.05 | 1.26 |
| Triethanolamine | 0.5 | 0.5 | 0.6 |
| Propylene Glycol | 2.35 | 2.35 | 2.82 |
| Water | 39.1 | 39.1 | 46.92 |
| Methylparaben | 0.25 | 0.25 | 0.3 |
| Propylparaben | 0.25 | 0.25 | 0.3 |
| Sulfur (75 Mesh) | 50.00 | — | — |
| Sulfur (200 Mesh) | — | 50.00 | 40.00 |

Preparation No. 1 uses a relatively coarse sulfur, and the sulfur is fifty percent of the preparation by weight. Preparation No. 2 uses a relatively fine sulfur, also in the proportion of fifty weight percent sulfur. Preparation No. 3 also uses a relatively fine sulfur, but uses a preparation with forty percent sulfur by weight. Each of these preparations exhibits the desirable properties of treatment for dermatitic conditions. The active ingredient in each preparation is the sulfur; the other ingredients are simply part of the composition of the Lubriderm lotion that was used as the spreadable carrier base for these experiments.

The composition, applied topically, is effective in treating several different skin disorders, but is noted as being particularly effective in treating keloids and hypertrophic scars and the accompanying discomfort. Keloids are tumors of fibrous tissue that is actively growing. They result from trauma or irritation, and it is noted that members of dark-skinned races are particularly predisposed to developing keloids. The trauma or irritation leading to keloids may be as minor as an acne lesion. Itching and burning sensations may accompany the development of keloids.

Hypertrophic scars are generally raised, red, and indurated skin areas. These are usually noted following accidental trauma or surgery and take several months to subside.

It is preferred to use a spreadable carrier base that is easy to use and comfortable to the user. One such base is Lubriderm lotion; however, different users will find different levels of comfort and ease with different bases. Thus, it will be readily apparent to one skilled in the art that other spreadable carrier bases, such as gels, salves, creams, other lotions, ointments, soaps, oils, and dusting powders, may be used to carry the high concentration of sulfur to the dermatitic condition. The use of a different carrier base for the sulfur is not important to the inventive step of using a preparation containing sulfur in at least approximately forty weight percent for a topical application for treatment of dermatitic conditions.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A topical composition for treatment of dermatitic conditions, comprising sulfur in a spreadable carrier base, the composition being at least approximately forty weight percent sulfur.

2. The topical composition of claim 1, wherein the sulfur is suspended in the spreadable carrier base.

3. The topical composition of claim 1, wherein the sulfur and carrier base form a mixture.

4. The topical composition of claim 1, wherein the sulfur is flowers of sulfur in natural, powdered, elemental form.

5. The topical composition of claim 1, wherein the spreadable carrier base comprises a lotion.

6. The topical composition of claim 1, wherein the spreadable carrier base comprises a gel.

7. The topical composition of claim 1, wherein the spreadable carrier base comprises a cream.

8. The topical composition of claim 1, wherein the spreadable carrier base comprises an ointment.

9. The topical composition of claim 1, wherein the spreadable carrier base is a powder.

10. The topical composition of claim 1, wherein the sulfur and base composition comprises approximately fifty weight percent sulfur.

11. The topical composition of claim 10, wherein the sulfur is flowers of sulfur in natural, powdered, elemental form.

* * * * *